United States Patent
Wang et al.

(10) Patent No.: US 8,946,384 B2
(45) Date of Patent: Feb. 3, 2015

(54) POLYPEPTIDE TF1 FOR INHIBITING TYPE 2 SHIGA TOXIN ACTIVITY, ENCODING GENE FOR SAME AND USE THEREOF

(75) Inventors: Hui Wang, Beijing (CN); Tao Li, Beijing (CN); Qin Wang, Beijing (CN); Wei Tu, Beijing (CN); Xiaojun Hou, Beijing (CN); Yuenan Liu, Shenyang (CN); Jing Shi, Beijing (CN); Kun Cai, Wuhan (CN)

(73) Assignee: Institute of Microbiology and Epidemiology, Academy of Military Medical Sciences, PR China, Beijing (CN)

( * ) Notice: Subject to any disclaimer, the term of this patent is extended or adjusted under 35 U.S.C. 154(b) by 0 days.

(21) Appl. No.: 13/814,689

(22) PCT Filed: Sep. 9, 2011

(86) PCT No.: PCT/CN2011/001541
§ 371 (c)(1),
(2), (4) Date: Apr. 15, 2013

(87) PCT Pub. No.: WO2012/037778
PCT Pub. Date: Mar. 29, 2012

(65) Prior Publication Data
US 2013/0210750 A1    Aug. 15, 2013

(30) Foreign Application Priority Data
Sep. 25, 2010    (CN) .......................... 2010 1 0290461

(51) Int. Cl.
C07K 7/08         (2006.01)
A61K 38/04        (2006.01)
C07K 14/25        (2006.01)
A61K 38/00        (2006.01)

(52) U.S. Cl.
CPC . C07K 7/08 (2013.01); C07K 14/25 (2013.01); A61K 38/00 (2013.01)
USPC ........................................ 530/327; 514/21.5

(58) Field of Classification Search
CPC ....... A61K 38/00; A61K 38/10; C07K 14/25; C07K 7/08
See application file for complete search history.

(56) References Cited

FOREIGN PATENT DOCUMENTS

| CN | 101016332 A | 8/2007 | |
|---|---|---|---|
| CN | 101948512 A * | 1/2011 | ............. A61K 38/10 |
| CN | 102040654 A | 5/2011 | |
| WO | WO 2007/110314 A2 * | 10/2007 | ............. C12N 15/82 |

OTHER PUBLICATIONS

Machine translation of CN 101948512 A, pp. 1-21, accessed Mar. 4, 2014.*
Nishikawa K, Matsuoka K, Watanabe M, et al., Identification of the optimal structure required for a Shiga toxin neutralizer with oriented carbohydrates to function in the circulation. J Infect Dis, 2005, 191: 2097-2105.
Natori Y. New drugs that prevent cytotoxicity of Shiga toxins. Nippon Rinsho. 2002, 60(6): 1131-1137, Abstract only.
Paton JC, Rogers TJ, Morona R, Paton AW. Oral administration of formaldehyde-killed recombinant bacteria expressing a mimic of the Shiga toxin receptor protects mice from fatal challenge with Shiga-toxigenic *Escherichia coli*. Infect Immun 2001, 69: 1389-1393.
Sheoran AS, Chapman-Bonofiglio S, Harvey BR, et al. Human antibody against shiga toxin 2 administered to piglets after the onset of diarrhea due to *Escherichia coli* O157: H7 prevents fatal systemic complications. Infect Immun 2005; 73:4607-4613.
Yuexi Li, Peitang Huang. Application of polypeptides in biological drugs and diagnosis reagents. Chinese Journal of Biochemical Pharmaceutics, 2001, 22 (4): 208-210, Abstract only.
Nishikawa K, Watanabe M, Kita E, et al. A multivalent peptide library approach identifies a novel Shiga toxin inhibitor that induces aberrant cellular transport of the toxin. Faseb J 2006; 20:2597-2599.
Miura Y, Sakaki A, Kamihira M, Iijima S, Kobayashi K. A globotriaosylceramide (Gb3Cer) mimic peptide isolated from phage display library expressed strong neutralization to Shiga toxins. Biochem Biophys Acta 2006; 1760:883-889.
Tu W, Cai K, Gao X, Xiao L, Chen RC, Shi J, Liu H, Hou XJ, Wang Q, Wang H, Improved production of holotoxin Stx2 with biological activities by using single-promoter vector and an auto-induction expression system. Protein Expr. Purif. 2009, 67(2):169-174.
Shi-zhong B, Hui W, Jun Y, Hui-ying Y, Jing S, Screening of short peptides binding to StxB by phage-display library. Acta Microbiologica Sinica 2006, 46(5):749-752, Abstract only.
Zhaozhong H, Guofu S, Cuifen H, Screening inhibitor of Shiga toxin-receptor from phagedisplay peptide library. Science in China (Series C) 1999, 152-156, Abstract only.

* cited by examiner

*Primary Examiner* — Julie Ha
*Assistant Examiner* — Li Ni Komatsu
(74) *Attorney, Agent, or Firm* — Hoffmann & Baron, LLP (57) ABSTRACT

The present invention provides a polypeptide TF1 for inhibiting type-2 Shiga-toxin activity, an encoding gene for the same and use thereof. The present polypeptide is named TF1 (also known as P1); its amino acid sequence is shown in SEQ ID NO: 1 in the sequence list. The polypeptide P1 can be prepared into medicine for preventing and/or treating diseases caused by type-2 Shiga toxin or the pathogens which produce type-2 Shiga toxin.

5 Claims, 7 Drawing Sheets

POLYPEPTIDE TF1 FOR INHIBITING TYPE 2 SHIGA TOXIN ACTIVITY, ENCODING GENE FOR SAME AND USE THEREOF

This application is the U.S. National Phase of, and Applicants claim priority from, International Application Number, PCT/CN2011/001541 filed Sep. 9, 2011 and Chinese Patent Application No. 201010290461.9 filed Sep. 25, 2010, each of which is incorporated herein by reference in its entirety.

TECHNICAL FIELD

The present invention involves a polypeptide TF1 inhibiting the activity of type-2 Shiga toxin (Stx2), the gene encoding the same and the use thereof.

BACKGROUND

Shiga toxin (Stx), also known as Shiga-like toxin (Slt), is a class of bacterial exotoxins having enterotoxicity, cytotoxicity and neurotoxicity. It is produced by enteric pathogens and divided into type-1 and type-2 (Stx1 and Stx2). Stx, as the key virulence factor of enteric pathogens such as *Shigella dysenteriae*, *Vibrio cholera* and *Escherichia coli*, may lead to several serious complications such as hemorrhagic colitis (HC), thrombotic thrombocytopenic purpura (TTP) and hemolytic uremic syndrome (HUS) which has a high fatality rate. Both of epidemiological and clinical data have demonstrated that Stx2 is more correlated with infectious complications especially HUS than Stx1 and thus regarded as the target for drugs.

At present, as for the infection caused by Stx-producing pathogens, there is not any specific and effective prophylactic or therapeutic drug for the first-aid treatment. Antibiotics commonly used in clinical treatment have given rise to the emergence of multiple drug-resistant bacterial strains, making such therapies noneffective. More seriously, the use of antibiotics may trigger the excessive release of Stx due to the rupture of bacteria, further increasing the risk of developing complications. Therefore, antibiotics should be used with cautions in the treatment of Stx-associated diseases and a specific drug should be developed as a novel effective method.

Stx2 (also known as Slt2) is composed of a single A subunit (Stx2A) and five B subunits (Stx2B). The Stx2B binds to globotriaosylceramide (Gb3) receptor on the surface of eukaryotic cells, and then Stx2A binds to 28S rRNA to cause cytopathy. Therefore, the binding of Stx2B to receptor Gb3 is the initial key step for toxicity. If such binding is blocked, the toxicity of Stx2 can be substantially inhibited. Studies have been mainly focused on the toxin receptor analogues and antibody therapy. Nishikawa reported that polysaccharide compounds which could bind to Stx had a potential therapeutic value (Nishikawa K, Matsuoka K, Watanabe M, et al., Identification of the optimal structure required for a Shiga toxin neutralizer with oriented carbohydrates to function in the circulation. J Infect Dis, 2005, 191: 2097-2105). Natori Y. also reported a treatment case associated with receptor Gb3 in 2002 (Natori Y. New drugs that prevent cytotoxicity of Shiga toxins. Nippon Rinsho. 2002, 60(6): 1131-1137) involving a new preparation that prevents the spread of toxin in gastrointestinal tract and a water-soluble preparation which suppresses Stx cytotoxicity in the circulation. However, the complex preparation process and side-effects of receptor-based polysaccharide compounds have restricted their development. Recently, some researchers reported that probiotics expressing a mimic of the receptor could be used in the treatment of Stx-associated diseases due to its significant neutralizing effect on the toxin (Paton J C, Rogers T J, Morona R, Paton A W. Oral administration of formaldehyde-killed recombinant bacteria expressing a mimic of the Shiga toxin receptor protects mice from fatal challenge with Shiga-toxigenic *Escherichia coli*. Infect Immun 2001, 69: 1389-1393). However, whether this approach is safe or not needs to be further tested. As for the antibody therapy, the monoclonal antibody reported by Sheoran et al. can block the binding between Stx2 and cell receptors and further neutralize the toxicity of Stx2 (Sheoran A S, Chapman-Bonofiglio S, Harvey B R, et al. Human antibody against shiga toxin 2 administered to piglets after the onset of diarrhea due to *Escherichia coli* O157: H7 prevents fatal systemic complications. Infect Immun 2005; 73:4607-4613). However, it can be clinically used only if preparation technology of antibodies is improved.

As a drug, a peptide compound is gaining more and more attentions due to its technical advantages such as the small molecular weight, relatively simple structure, mass production with low costs by chemical synthesis or genetic engineering methods, identified functions, low immunogenicity, slight side-effects, high security, diversity of administration routes and easy absorption. Thus, small-molecule peptides have become one of the most important sources for drug screening (Yuexi Li, Peitang Huang. Application of polypeptides in biological drugs and diagnosis reagents. Chinese Journal of Biochemical Pharmaceutics, 2001, 22 (4): 208-210). It is feasible to use a phage peptide library which contains a large quantity of peptides to screen for polypeptides having inhibitory effects on a toxin. However, peptide-based inhibitor against Stx has been rarely reported recently. The related literatures are mainly studies of Nishikawa K in 2006 (Nishikawa K, Watanabe M, Kita E, et al. A multivalent peptide library approach identifies a novel Shiga toxin inhibitor that induces aberrant cellular transport of the toxin. Faseb J 2006; 20:2597-2599) and studies of Miura Y (Miura Y, Sakaki A, Kamihira M, Iijima S, Kobayashi K. A globotriaosylceramide (Gb3Cer) mimic peptide isolated from phage display library expressed strong neutralization to Shiga toxins. Biochem Biophys Acta 2006; 1760:883-889).

SUMMARY OF INVENTION

The aim of the present invention is to provide a polypeptide which inhibits the activity of type-2 Shiga toxin.

The polypeptide of the present invention is named TF1 (also called P1) and its amino acid sequence is represented by SEQ ID NO: 1 in the sequence list.

Another aim of the present invention is to provide a modified polypeptide.

The modified polypeptide provided herein is obtained by chemically or biologically modifying the above-mentioned TF1 at its N terminal and/or C terminal.

Further, the chemical modification can be acetylation or aminoacylation.

The modified peptide can be a linear peptide or a branched peptide.

The gene coding the above polypeptide is also embodied in the protection scope of this invention.

The recombinant vector, recombinant bacteria or transgenic cell line containing the gene above is also embodied in the protection scope of this invention.

The use of the above-mentioned polypeptide or modified peptide in the preparation of drugs for preventing and/or treating diseases caused by Stx2 or Stx2-producing pathogens is also embodied in the protection scope of this invention.

The pathogens mentioned above are Stx2-producing *Escherichia coli, Shigella dysenteriae* or *Vibrio cholerae* strains.

Specifically, the Stx2-producing *Escherichia coli* is Enterohemorrhagic *E. coli* O157.

BRIEF DESCRIPTION OF THE DRAWINGS

FIGS. 1A and 1B show the mass analysis result of synthesized peptide TF1 (also called P1), wherein

FIGS. 2A and 2B show the mass analysis (at 220 nm) result of synthesized peptide WA8 (also called P8), wherein

FIGS. 4A and 4B are graphs showing binding dynamics between the polypeptides and Stx2, wherein the BIAcore system dynamically analyzes the specific binding between Stx2 and TF1 (also called P1) (or WA8 which is also called P8). The lowest curve represents the lowest concentration and the highest curve represents the highest concentration. The concentration of P1 in FIG. 4A (KD: 1.25e-6) ranges from 0.96 to 15.38 μmol/L and the concentration of P8 in FIG. 4B (KD: 2.48e-5) ranges from 2.44 to 39.125 μmol/L, suggesting that polypeptides TF1 and WA8 can specially bind to Stx2 in a dose dependent manner.

FIG. 5 shows the inhibitory effect of TF1 (also called P1) and WA8 (also called P8) on cytotoxicity in vitro observed by a light microscope (×200). Hela cells are added after incubation. A: Control group (PBS). B: Stx2 group. C: Stx2+ polypeptide (P1 or P8).

FIG. 6 shows the protective effect of the polypeptide against 5LD50 in mice. The mice were intraperitoneally administered with polypeptide and then 20 minutes later with Stx2 (5LD50). FIG. 6A shows the effect of P1 and FIG. 6B shows the effect of P8, both polypeptides being administered in the range of 0.7 mg/kg-11 mg/kg.

DETAILED DESCRIPTION OF THE INVENTION

The present invention will be further described in combination with the following specific examples but the present invention is not limited to these examples.

The methods used in the examples are common ones if not indicated otherwise.

Example 1

Modification, Chemical Synthesis and Binding Activity Analysis of the Polypeptides TF1 (also Called P1) and WA8 (also Called P8)

1. Modification and Synthesis of the Polypeptides TF1 (Also Called P1) and WA8 (Also Called P8)

1) Screening for the Sequences of TF1 and WA8

Preparation of Stx2B: The stx2B gene was amplified from *E. coli* EHEC O157: H7 (purchased from ATCC) using 5'-catatggctaaaggtaaaattgag-3' SEQ ID NO. 3 and 5' gcggc-cgcgcctcagtcatcagtcatt-3' SEQ ID NO. 4 as primers. The amplified fragment was sequenced in pEASY-T1 and its nucleotide sequence was confirmed to be No. 1353327-1353533 of the nucleotide of Genbank NC_002655. Subsequently, the amplified product was inserted into pET22b+ (purchased from Novagen) digested with restriction endonucleases Nde I and Not I to construct a recombinant plasmid pET22b-stx2B. The plasmid pET22b-stx2B was transformed into *E. coli* BL21 (DE3) strain (purchased from Transgen) to obtain a recombinant strain pET22b-stx2B/BL21 (DE3). Clones of the recombinant strain were propagated in LB medium containing 100 μg/mL of ampicillin and incubated in water bath at 37° C. with shaking overnight. Then, the culture was subcultured into erlenmeyer flasks in a ratio of 1:100 to further grow the strains. When the culture grew to OD600 of 0.6, IPTG was added to a final concentration of 1 mmol/L. The inducible expression continued for 5 hours, leading to the effective expression of Stx2B. Cells were treated by ultrasonication and then centrifuged at 10,000 r/min for 10 min. Inclusion bodies were collected and dissolved in 6 mol/L guanidine hydrochloride in PBS. Thereafter, denatured proteins were transferred into a dialysis bag and dialyzed in a series of Tris buffer (10 mmol/L Tris, 1 mmol/L EDTA, 0.3 mol/L arginine, 1 mmol/L reduced glutathione, 0.25 mmol/L oxidized glutathione, 10% of glycerol, 50 mmol/L NaCI, pH 8.0) with decreasing concentrations of urea (6, 4, 2, 1, 0 mol/L). The last buffer for dislysis was 10 mmol/L Tris, pH 8.0. Denatured proteins were purified via linear elution using a Q Sepharose column with 10 mmol/L Tris-1 mol/L NaCI as the eluent. The details of this experiment has been published (Tu W, Cai K, Gao X, Xiao L, Chen R C, Shi J, Liu H, Hou X J, Wang Q, Wang H, Improved production of holotoxin Stx2 with biological activities by using a single-promoter vector and an auto-induction expression system. Protein Expr. Purif. 2009, 67(2):169-174).

Phage display was used to screen for polypeptides specifically binding to Stx2B from the random linear twelve-mer peptide library based on their affinity to the recombinant Stx2B. Two sequences most frequently occurred were picked up from the screened peptides and named TF1 (also P1) and WA8 (also P8). Subsequently, the physicochemical properties of TF1 and WA8 were predicted by the protparam tool (<www.expasy.org/tools/protparam.html>). The results indicated that TF1 was composed of 12 amino acids and could be represented by the formula of $C_{77}H_{101}N_{17}O_{18}S_1$, wherein the molecular weight was 1584.8 and the theoretic pl was 5.19. In addition, WA8 was found to be composed of 12 amino acids and could be represented by the formula of $C_{79}H_{96}N_{16}O_{18}$, wherein the molecular weight was 1557.7 and the theoretic pl was 6.74.

2) Chemical Modification and Synthesis In Vitro

The polypeptides TF1 and WA8 were acetylated at N-terminal without changing their primary structures, which would improve the water-solubility and stability. Such a chemical modification was done by Shanghai Biotech Bioscience & Technology Co., Ltd. The peptides were synthesized by solid phase synthesis and then subjected to perform mass spectra and HPLC. As shown in FIG. 1 and FIG. 2, the molecular weight of TF1 was 1584.9 (FIG. 1A, mass spectra) which conformed with the theoretical value and its purity was 95.1% (FIG. 1B, HPLC); the molecular weight of WA8 was 1557.7 (FIG. 2A, mass spectra) which substantially conformed with the theoretical value and its purity was 95.3% (FIG. 2B, HPLC).

The amino acid sequence of TF1 (also called P1) was represented by SEQ ID NO. 1 in the sequence list and that of WA8 (also called P8) was represented by SEQ ID NO. 2.

2. Analysis of Binding Activity of Polypeptides TF1 (Also Called P1) and WA8 (Also Called P8)

The biosensor system BIAcore 3000, CM5 chip and corresponding reagents were purchased from GE and the HRPconjugated anti-histidine antibody was purchased from Pierce (ELISA titer: 1:2000). *Escherichia coli* BL21 (DE3) plysS Chemically Competent Cell, *E. coli* DH5a and pEASY-T1 simple cloning vector were purchased form Beijing Trans-Gen Biotech (China). Taq DNA polymerase, T4 DNA ligase and restriction endonucleases were obtained from New England Biolabs (Beijing, China). PCR primers were synthesized by Beijing Sunbio Tech Co. Ltd. Plasmid mini-kit and Gel extraction kit were purchased from Beijing Biomed Co. Ltd. HisTrap FF column (5 ml) were purchased from GE Healthcare (Beijing, China). Weight 8-10 kDa cut-off dialysis membrane tubing was purchased from Beijing Kehaijunzhou Biotechnology Development Center. The expression vector pET32a was purchased from Novagen.

1). Enzyme-Linked Immunosorbent Assay (ELISA) Analysis of Interaction Between the Polypeptides and Stx2B.

The ELISA microtiter plates were coated overnight with a gradient concentration of polypeptides at 4° C. (BSA as a negative control) and washed with PBST. Then it was blocked with 3% BSA for 1 hour and washed with PBST. Stx2B prepared in step 1 was added and then incubated at 37° C. for 1 hour. Following PBST washing, anti-histidine antibody was used to test Stx2B which bound to the polypeptides. After the colorimetric reaction, the absorption at 450 nm was recorded. As shown in FIG. 3, as the concentration of polypeptide (P1 or P8) increased, the amount of polypeptides binding to Stx2B increased gradually. More P1 bound to Stx2B than WA8 at the same concentration.

2). Surface Plasmon Resonance Technology (SPR)-Based Kinetics Analysis of the Specific Binding of TF1 and/or WA8 to Stx2

Preparation of Stx2: The stx2 gene was amplified from *E. coli* EHEC O157: H7 using 5'-GGGGGGAATTCATGAAGTGTATATTATTTAAATGGG-3' SEQ ID NO. 5 (primer 1) and 5'-TTTTTTGTCGACTTAGTGGTGGTGGTGGTGGTGGTCATTATTAAACTGCACTT CAG-3' SEQ ID NO. 6 (primer 2) as primers. The amplified fragment was subjected to sequencing in pEASY-T1 and its nucleotide sequence was confirmed to be No. 1353327-1353533 of the nucleotide of Genbank NC_002655. A recombinant strain pET32a-stx2/plysS was constructed, which contained two open reading frames with a single promoter. Specifically, the amplified product was inserted into pET32a digested with restriction endonucleases EcoR I and Sal Ito construct a recombinant plasmid pET32a-stx2. Then this plasmid was transformed into *E. coli* BL21 (DE3) plysS strain (purchased from Transgen) to obtain a recombinant strain pET32a-stx2/plysS.

The recombinant plasmid pET32a-stx2 had one T7 promoter and the full-length clone of stx2 contained two open reading frames (stx2a and stx2b). IPTG was added to a final concentration of 1 mmol/L. Thereafter, the cells were cultivated at 30° C. for 5 hours in water bath while shaking, leading to the highly effective expression of Stx2. Stx2 with 90% purity or more was obtained after treatment in HisTrap Ni column and the Stx2 showed a biological activity. Details of related experiments have been published (Tu W, Cai K, Gao X, Xiao L, Chen R C, Shi J, Liu H, Hou X J, Wang Q, Wang H, Improved production of holotoxin Stx2 with biological activities by using a single-promoter vector and an auto-induction expression system. Protein Expr. Purif. 2009, 67(2):169-174).

The specific binding of the polypeptides to the prepared Stx2 was tested by using surface plasmon resonance (SPR) technology in BIAcore biosensor system. Specifically, Stx2 (2235.9 RU) was coupled to the Fc4 in CM5 chip, activated by EDC/NHS and blocked by ethanolamine. The binding kinetics between polypeptides of different concentrations (double diluted) and Stx2 was detected and was then shown in curves. Detection was performed at 20 μL/min and the dynamic binding process of polypeptides (TF1 or WA8) to Stx2 was observed from Sensorgrams. Analysis was performed by BIAevaluation 3.0, Ka and Kd were respectively obtained from the association and dissociation parts of the curve. The data was quite different for polypeptides of different concentrations. Ka, Kd, KA and KD were calculated based on analysis reports according to the following formulae:

$$R\text{max}=(MW_{analyte}/MW_{ligand})\times R_{ligand}\times S_{valence} \quad (1)$$

$$Ka=(dR/dt)/t \quad (2)$$

$$Kd=(dt/dR)/R \quad (3)$$

$$DK=Kd/Ka=C\times(R\text{max}-Req)/Req \quad (4)$$

R: SPR signal at a time point (unit: RU). Req: Analyte stable binding level (unit: RU). Rmax: Peptide maximum binding capacity. t: time. dR/dt: SPR signal conversion rate. C: Peptide concentration.

As shown in FIG. 4, the concentration of P1 ranged from 0.96 to 15.38 μM and that of P8 ranged from 2.44 to 39.125 μM. The affinity constant KD for P1 binding to Stx2 was calculated to be $1.25\times10^{-6}$M and that for P8 binding to Stx2 was $2.48\times10^{-5}$ M.

Example 2

Inhibitory Effect of TF1 or WA8 on Cytotoxicity in vitro and Blocking Effect of TF1 or WA8 on the Binding of Toxin to Target Cells Hela cells, pancreatin and antibodies were purchased from Hyclone Laboratories Inc., DMEM medium, fetal bovine serum, MTT and FITC were respectively from GIBCO Inc., Biochorm Ltd., sigma Inc. and Laibao Inc. Cell culture flasks and plates were purchased from CORNING Inc. $CO_2$ incubator, inverted microscope, flow cytometer were respectively the products of Sanyo Inc. (Japan), Olympus Inc. (Japan) and Coulter Inc.

1. Cytotoxicity Neutralization Assay

Hela cells at logarithmic phase were collected whose concentration was then adjusted to a certain extent. 100 μl of cell culture was injected into 96-well microtiter plates and the density of cells in each well was adjusted to $10^4$/well (wells at periphery were filled with sterile PBS). Plates were incubated overnight at 37° C. with 5% $CO_2$. Subsequently, 100 μl of polypeptides (having a final concentration of 150 μM) were mixed with 2.5 ng of Stx2 (5CD50). Thereafter, the mixture was incubated at 4° C. overnight. Meanwhile, two control groups were arranged, one added with only PBS as the normal control and the other added only with Stx2. The mixture was added into cells cultivated in 96-well microplates and incubated in 5% $CO_2$ at 37° C. for 72 hours, and then cells were observed using inverted microscope. Culture fluid was discarded and cells were washed carefully with PBS for 2-3 times. 50 μl of MTT (5 mg/ml) was added into each well and cultivation continued for another 4 hours. Subsequently, culture fluid was carefully discarded and 150 μl of DMSO was added in each well. Plates were gently shaked in a shaker for 5 min so that crystals were sufficiently dissolved. Absorbance was measured at $OD_{570}$ using a microplate reader. The inhibition rate was calculated according to the following formula: Inhibition rate %=($OD_{570}$(peptide+Stx2)−$OD_{570}$(Stx2))/($OD_{570}$(normal control)−$OD_{570}$(Stx2)). As shown in FIG. 5, the inhibition rate of P1 was higher than that of P8 if their concentrations were the same. When Stx2 (5×CD50) was added in an amount exceeding the lethal dose, the IC50 (half maximal inhibitory concentration) of P1 was 180 μM and that of P8 was 193 μM. In addition, the inhibition rate reached 82% when the concentration of P1 was 300 μM and the inhibition rate was 54% when the concentration of P8 was 300 μM.

2. Analysis on the Effect of Polypeptide on the Binding of Stx2B to Cells by Flow Cytometry The HeLa cell selected was Gb3$^+$ cell and Stx2B was the receptor binding site of Stx2. Stx2B specifically bound to HeLa cell via receptor Gb3. Based on such cell model, the blocking effect of the polypeptide on the binding of Stx2B to HeLa cells can be tested. FITC-Stx2B was prepared by labeling Stx2B with fluorescein FITC. Specifically, the purified Stx2B mentioned above was dialyzed in a carbonate buffer (pH9.2) and FITC in DMSO was added (0.05 mg FITC/1 mg protein). The mixture was stirred for 2 hours in dark at RT and dialyzed in a phosphate buffer (pH7.2) during which buffer was renewed until no FITC came out. Thereafter, the prepared FITC-Stx2B (5 μg) was mixed with polypeptide (100 μl, final concentration: 300 μM) and then incubated at 4° C. overnight (keep in dark). After about 10$^6$ of cells were added, incubation continued at 37° C. for 2 hours and the mixture was centrifuged at 1000 r/min for 5 min. Subsequently, cells were washed with PBS for two times and then fixed with 40% paraformaldehyde at 4° C. for 10 min. After centrifugation, some cells were suspended in PBS and then detected by flow cytometry. The remaining cells were suspended in PBS and the binding profile of FITC-Stx2B to Hela cells was analyzed by flow cytometry. Three groups were contained in this experiment: negative control group (PBS), FITC-Stx2B group and FITC-Stx2B+polypeptide group. Results (data not shown) demonstrated that 97.22% of HeLa cells treated with FITC-Stx2B showed fluorescence and 52.77% of Hela cells incubated with FITC-Stx2B+polypeptide TF1 (also called P1) showed fluorescence. Thus, TF1 (also called P1) (300 μmol/L) blocked 45.7% of binding between FITC-Stx2B and HeLa cells. The blocking rate of WA8 (also called P8) (300 μmol/L) was 24.8%.

Example 3

Protective Effect of the Polypeptide (TF1 or WA8) Against Stx2 in Mice

Male Balb/C mice (17-19 g) were provided by the Laboratory Animal Center of the Academy of Military Medical Sciences. TF1 (also called P1, purity>95%, gram) and WA8 (also called P8, purity>95%, gram) were used in this experiment.

I. Protective Effect of the Polypeptide (TF1 or WA8) Against Stx2 Lethality in a Mice Model 1. Preparation of Crude Stx2

*E. coli* O157 (purchased from ATCC) capable of expressing Stx2 was inoculated to LB medium and cultured overnight at 37° C. The culture was diluted in a ratio of 1:100 in 1 L of medium the next day and cultured with shaking for another 72 hours. The culture was centrifuged at 5000 rpm for 10 min. Then, the gathered cells were suspended in PBS and ruptured by ultrasonic waves. After being centrifugated at 10,000 rpm for 10 minutes, a solution of saturated ammonium sulfate was added into the supernatant until reaching a concentration of 50%. Subsequently, the precipitate was gathered and dissolved in PBS. After a complete dialysis, a crude product of Stx2 was obtained.

2. Inhibition Effect of TF1 and WA8 on Stx2 In Vivo

Figure 1A:
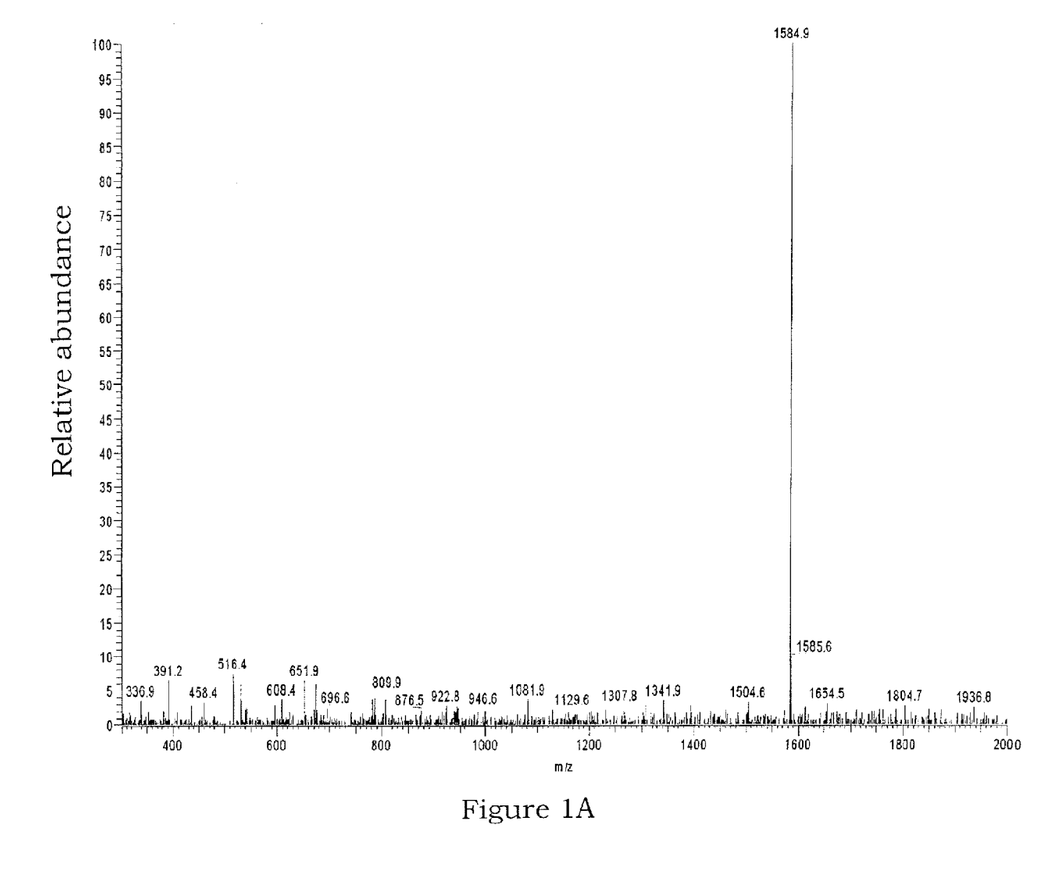
FIG. 1A shows the image of mass spectrometry and FIG. 1B shows the image of high performance liquid chromatography (HPLC).
Figure 1B:
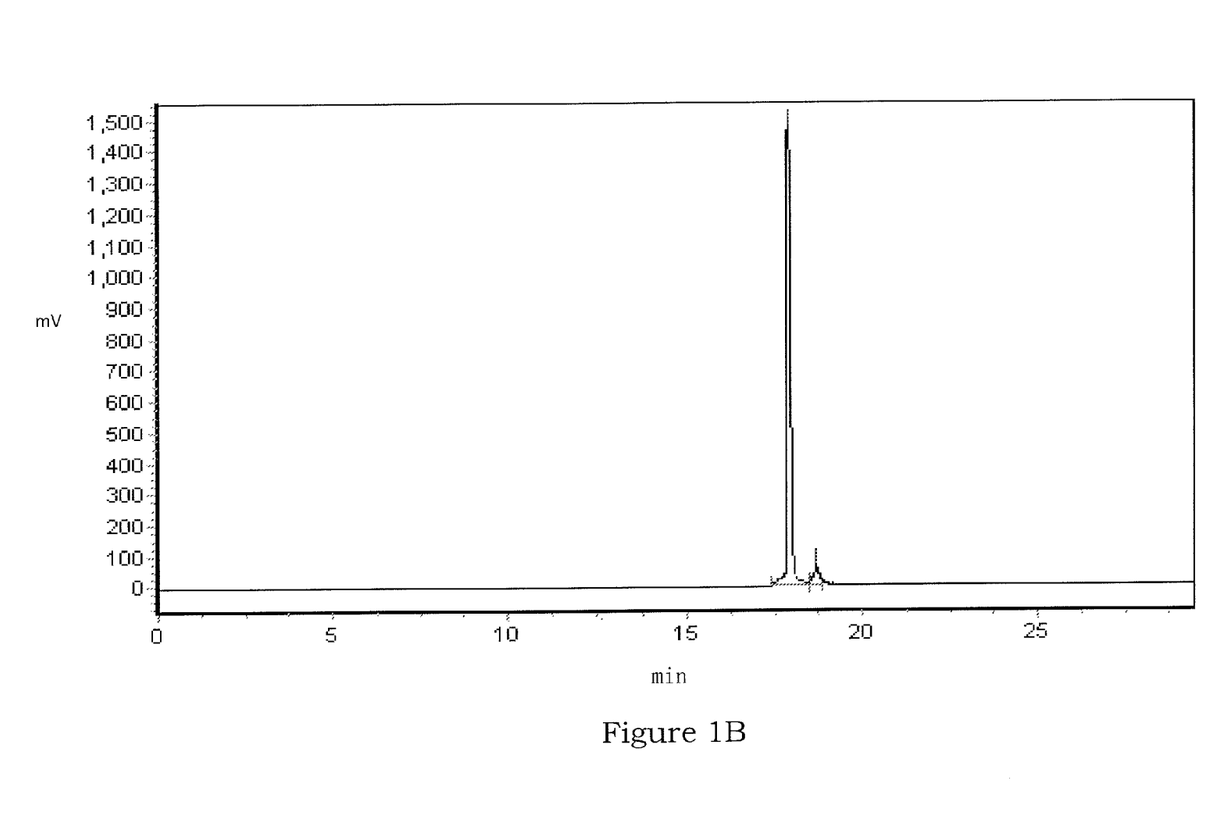
Figure 2A:
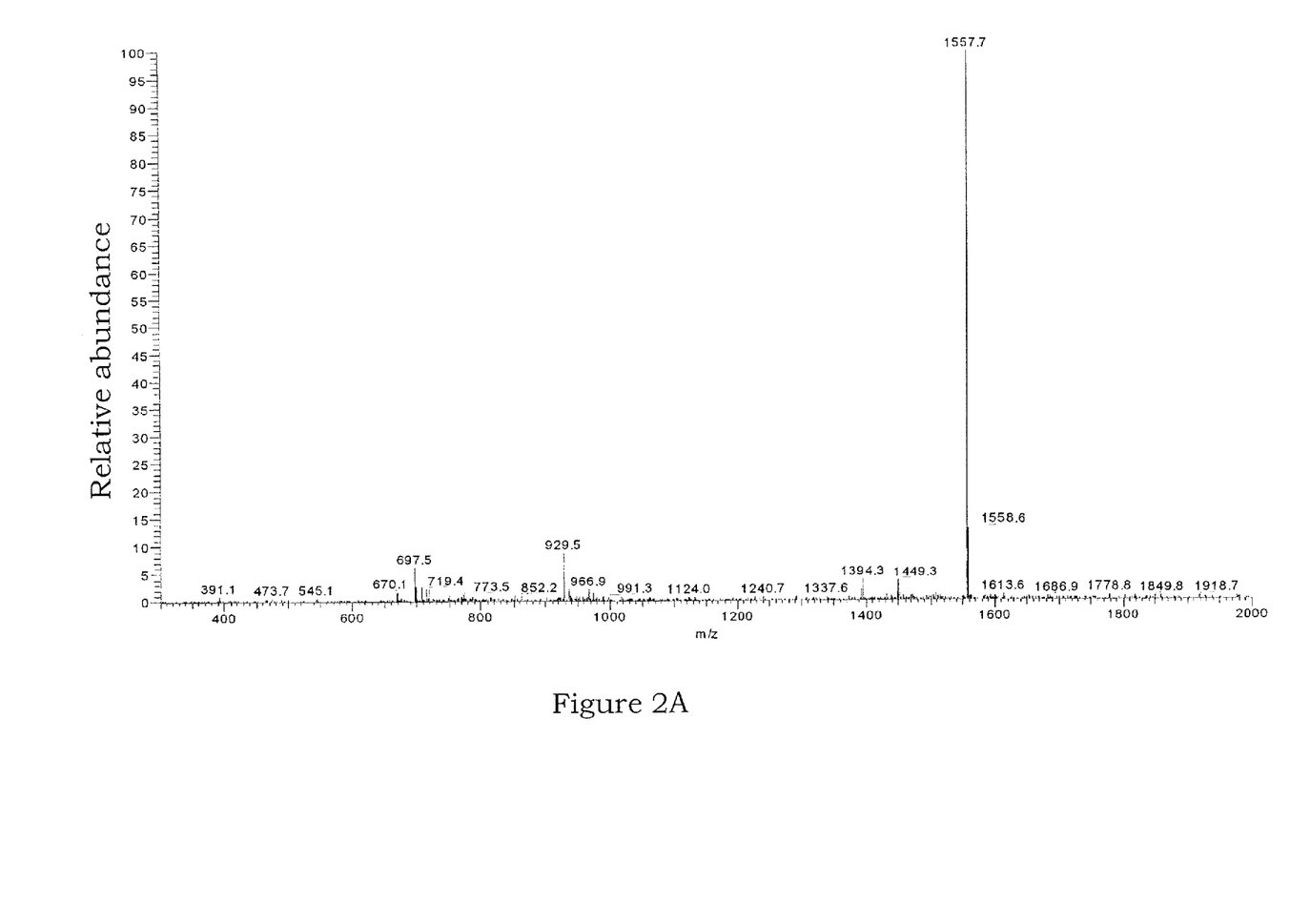
FIG. 2A shows the image of mass spectrometry and FIG. 2B shows the image of high performance liquid chromatography.
Figure 2B:
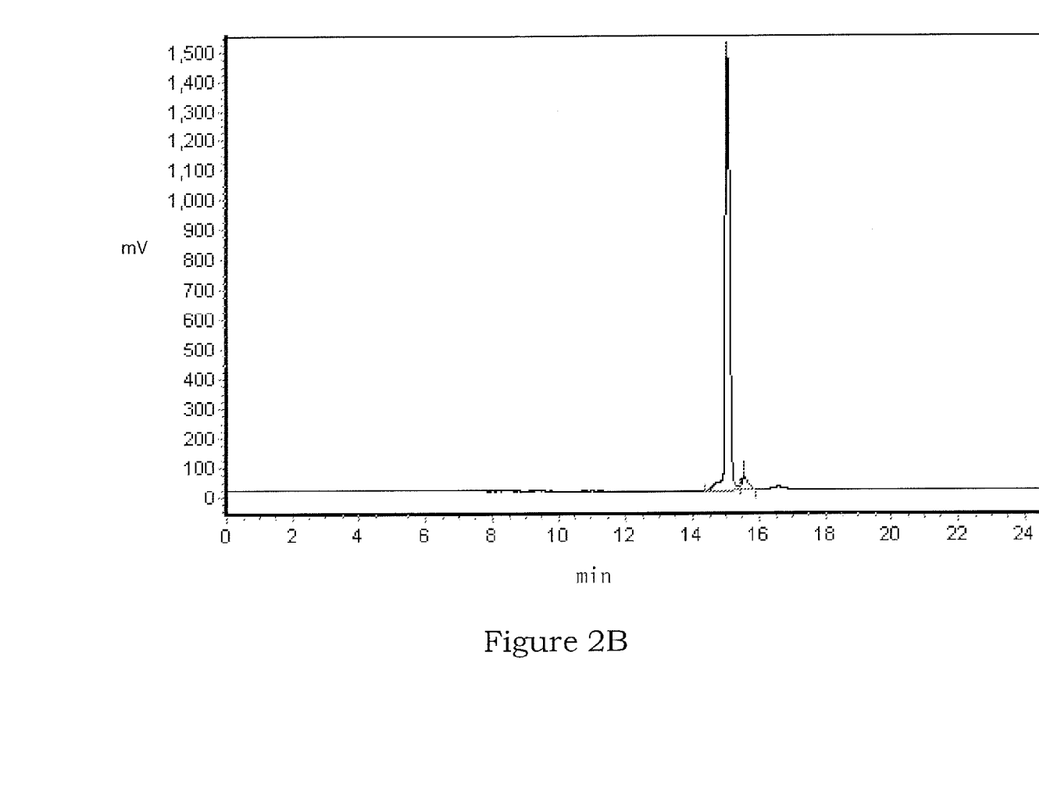
Figure 3:
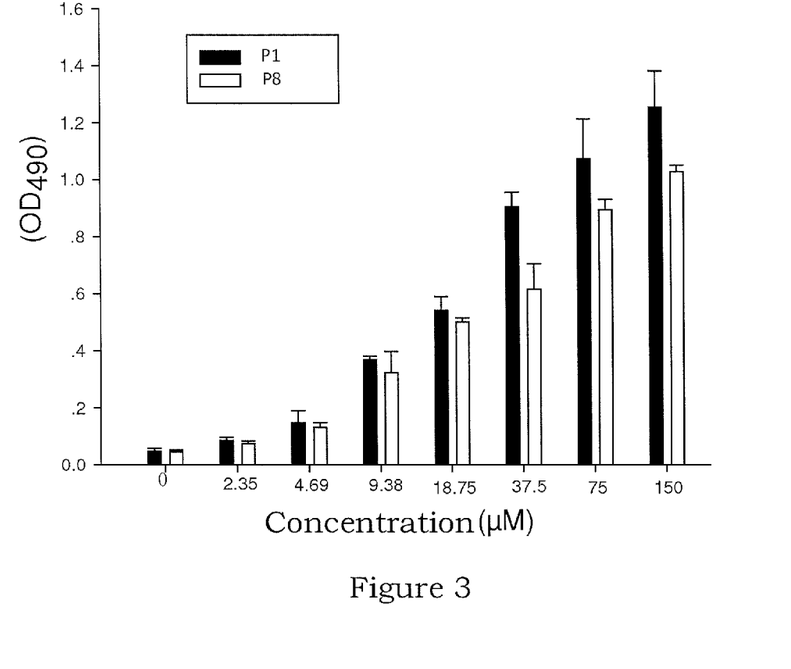
FIG. 3 shows the binding profile between Stx2B and a gradient concentration of polypeptides (P1, P8). The binding amount gradually increases as the concentration of P1 (or P8) increases.
Figure 4:
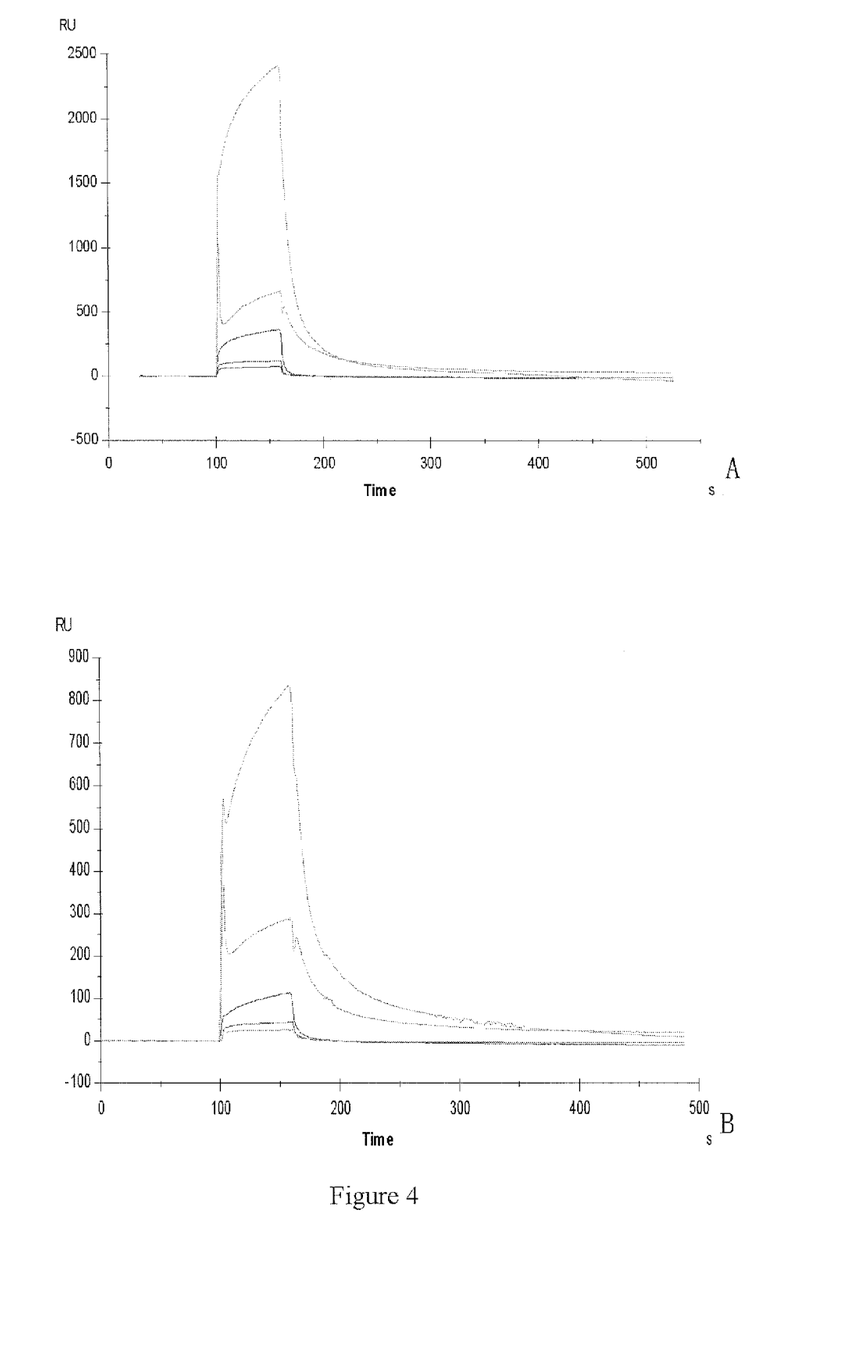
Figure 5:
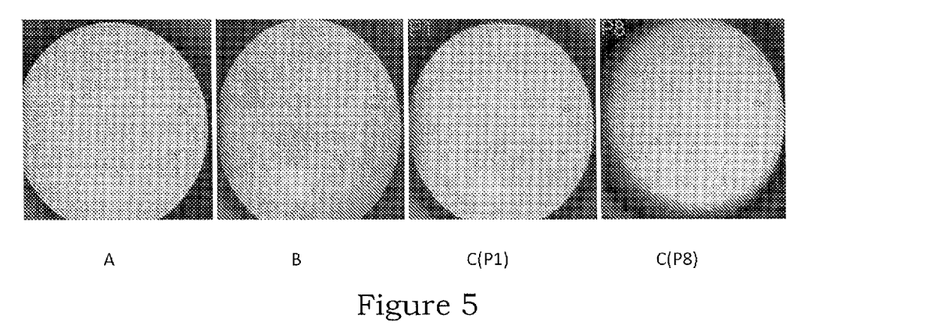
Figure 6:
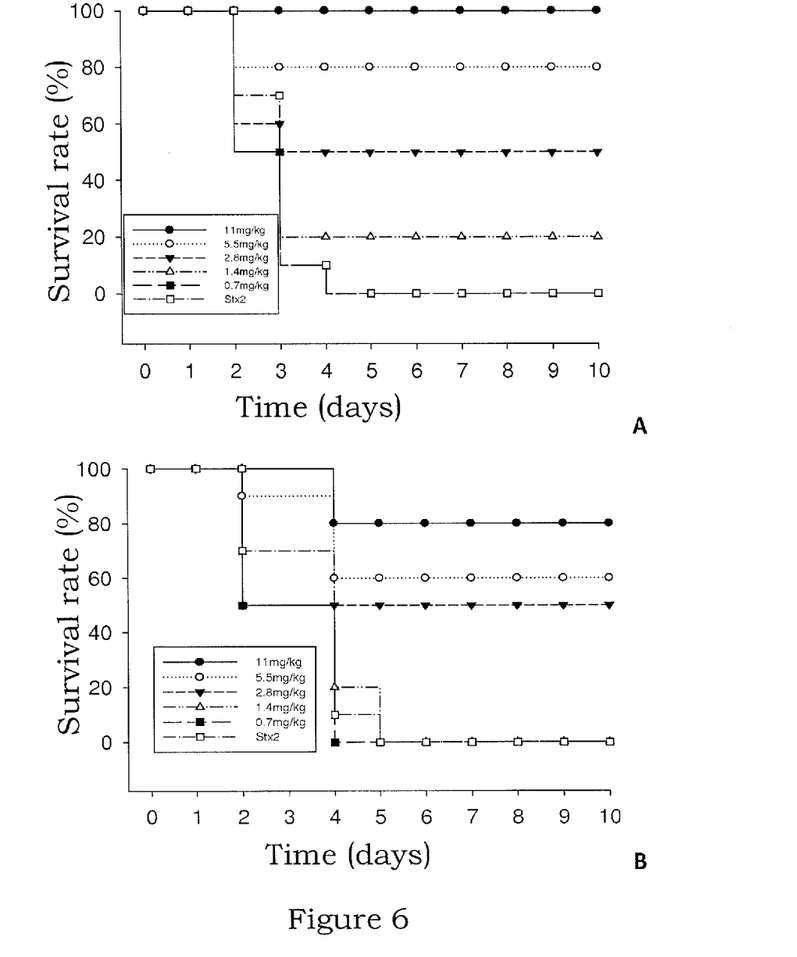

The male Balb/C mice (17-19 g) were randomly divided to six groups, each group comprising 20 mice. TF1 (also called P1) or WA8 (also called P8) was intraperitoneally injected into mice. Twenty minutes later, mice were challenged with 50 ng of crude Stx2 (5LD50) by intraperitoneal injection. A placebo control group (see FIG. 6, Stx2) was injected with saline prior to challenging with 50 ng of crude Stx2 by intraperitonial injection. Observation lasted for 10 days and the survival of each group was recorded twice a day. As shown in FIG. 6, all the animals in the placebo control group died in Day 4 or Day 5. However, different doses of polypeptide (P1 or P8) provided different extents of protection effect to mice. P1 could totally protect the mice when the dose reached 11 mg/kg (see FIG. 6A) and P8 exhibited 80% protection rate at the same concentration (FIG. 6B). P1 or P8 exhibited a dose-dependent protection effect. P1 showed a better protection capacity than P8 when Stx2 was added in an amount exceeding the lethal dose.

INDUSTRIAL APPLICATIONS

The experiments proved that more P1 bound to Stx2 as the concentration of P1 increased. And the affinity constant KD of P1 to Stx2 was $1.25 \times 10^{-6}$ M. It was found in the experiment of cytotoxicity neutralization that the inhibition rate to Stx2 reached 82% when the concentration of P1 was 300 μM. Further, TF1 (also called P1) (300 μmol/L) blocked 45.7% of binding of FITC-Stx2B to HeLa cells. In the animal experiment, all the animals in the placebo control group died in Day 4 or Day 5. However, different doses of polypeptides (TF1 or WA8) provided different extents of protection effect to mice. P1 could totally protect mice when the dose reached 11 mg/kg (see FIG. 6A) and the polypeptide exhibited a dose-dependent protection effect.

INCORPORATION OF SEQUENCE LISTING

Incorporated herein by reference in its entirety is the Sequence Listing for the application. The Sequence Listing is disclosed on a computer-readable ASCII text file entitled "Sequence_listing_2302_2_PCTUS.txt" created on Jul. 25, 2014. The sequence text file, is 1.6 kilobyte size.

We claim:

1. A polypeptide comprising an amino acid sequence as set forth by SEQ ID NO. 1.

2. A modified polypeptide comprising the polypeptide of claim 1, with a modification to one or both of N-terminal and C-terminal.

3. The modified polypeptide of claim 2, wherein the modification is acetylation or aminoacylation.

4. The modified polypeptide of claim 2, wherein the modified polypeptide is a linear polypeptide or a branched polypeptide.

5. The modified polypeptide of claim 2, wherein the modification is chemical or biological.

* * * * *

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Sequence was synthesized
```

```
<220> FEATURE:
<221> NAME/KEY: PEPTIDE
<222> LOCATION: (1)..(12)

<400> SEQUENCE: 1

Thr Phe Asn Met Trp Leu Pro Thr Phe Asn Gln Trp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Sequence was synthesized
<220> FEATURE:
<221> NAME/KEY: PEPTIDE
<222> LOCATION: (1)..(12)

<400> SEQUENCE: 2

Trp Ala Pro Trp Tyr Ser Phe Thr Ser Tyr His Leu
1               5                   10

<210> SEQ ID NO 3
<211> LENGTH: 24
<212> TYPE: DNA
<213> ORGANISM: Artificial Sequence
<220> FEATURE:
<223> OTHER INFORMATION: Synthetic sequence

<400> SEQUENCE: 3
catatggcta aaggtaaaat tgag                                          24

<210> SEQ ID NO 4
<211> LENGTH: 27
<212> TYPE: DNA
<213> ORGANISM: Artificial Sequence
<220> FEATURE:
<223> OTHER INFORMATION: Synthetic sequence

<400> SEQUENCE: 4
gcggccgcgc ctcagtcatc agtcatt                                       27

<210> SEQ ID NO 5
<211> LENGTH: 36
<212> TYPE: DNA
<213> ORGANISM: Artificial Sequence
<220> FEATURE:
<223> OTHER INFORMATION: Synthetic sequence

<400> SEQUENCE: 5 gggggggaatt catgaagtgt atattattta aatggg                            36

<210> SEQ ID NO 6
<211> LENGTH: 56
<212> TYPE: DNA
<213> ORGANISM: Artificial Sequence
<220> FEATURE:
<223> OTHER INFORMATION: Synthetic sequence

<400> SEQUENCE: 6 tttttttgtcg acttagtggt ggtggtggtg gtggtcatta ttaaactgca cttcag      56
```